(12) United States Patent
Paik et al.

(10) Patent No.: US 12,417,849 B2
(45) Date of Patent: Sep. 16, 2025

(54) METHOD FOR IDENTIFYING ASSOCIATION BETWEEN DISEASE-RELATED FACTORS FROM DOCUMENT DATA, AND SYSTEM CONSTRUCTED USING SAME

(71) Applicants: Standigm Inc., Seoul (KR); SK HOLDINGS CO., LTD., Seoul (KR)

(72) Inventors: Young Sang Paik, Seoul (KR); Youngseog Yoon, Bucheon-si (KR); Ye Chan Ha, Hanam-si (KR); Chanung Jeong, Seoul (KR); Hee Jung Koo, Seongnam-si (KR); Tae Yong Kim, Yongin-si (KR)

(73) Assignees: Standigm Inc., Seoul (KR); SK HOLDINGS CO., LTD., Seoul (KR)

( * ) Notice: Subject to any disclaimer, the term of this patent is extended or adjusted under 35 U.S.C. 154(b) by 300 days.

(21) Appl. No.: 18/020,829

(22) PCT Filed: Jul. 19, 2021

(86) PCT No.: PCT/KR2021/009271
§ 371 (c)(1),
(2) Date: Feb. 10, 2023

(87) PCT Pub. No.: WO2022/035074
PCT Pub. Date: Feb. 17, 2022

(65) Prior Publication Data
US 2023/0326609 A1    Oct. 12, 2023

(30) Foreign Application Priority Data

Aug. 13, 2020  (KR) .................. 10-2020-0101764
Dec. 16, 2020  (KR) .................. 10-2020-0176766

(51) Int. Cl.
*G16H 50/70* (2018.01)
*G06F 40/295* (2020.01)
(Continued)

(52) U.S. Cl.
CPC .......... *G16H 50/70* (2018.01); *G06F 40/295* (2020.01); *G06F 40/30* (2020.01); *G16H 50/20* (2018.01)

(58) Field of Classification Search
CPC ........ G16H 50/70; G16H 50/20; G16H 50/50; G16H 70/60; G06F 40/295; G06F 40/30;
(Continued)

(56) References Cited

U.S. PATENT DOCUMENTS

2006/0053172 A1* 3/2006 Gardner .................. G06N 5/02
707/999.203
2008/0301174 A1* 12/2008 Mons ...................... G06F 16/36
707/999.102
(Continued)

FOREIGN PATENT DOCUMENTS

EP     3 550 568 A1    10/2019
JP     2002-269114 A    9/2002
(Continued)

OTHER PUBLICATIONS

Martin Krallinger et al., "Information Retrieval and Text Mining Technologies for Chemistry", Chem. Rev. 2017, vol. 117, pp. 7673-7761 (89 pages total).
(Continued)

*Primary Examiner* — Stella L. Woo
(74) *Attorney, Agent, or Firm* — Sughrue Mion, PLLC

(57) ABSTRACT

The present invention relates to a method capable of recognizing disease-related factors included in document data and extracting relations between the disease-related factors.

16 Claims, 7 Drawing Sheets

(51) Int. Cl.
  *G06F 40/30* (2020.01)
  *G16H 50/20* (2018.01)
(58) Field of Classification Search
  CPC ...... G06F 16/34; G06N 3/044; G06N 3/0464;
       G06N 3/082; G06N 3/045; G06N 3/09;
       G16B 50/10
  See application file for complete search history.

(56) References Cited

U.S. PATENT DOCUMENTS

| | | | |
|---|---|---|---|
| 2009/0070322 A1* | 3/2009 | Salvetti | G06F 16/338 |
| | | | 707/999.005 |
| 2015/0112664 A1* | 4/2015 | Srinivasan | G06F 40/30 |
| | | | 704/9 |
| 2019/0005049 A1* | 1/2019 | Mittal | G06F 16/3347 |
| 2019/0006027 A1* | 1/2019 | Sacaleanu | G16H 50/30 |
| 2019/0188324 A1* | 6/2019 | Zhao | G06F 16/90328 |
| 2020/0176098 A1 | 6/2020 | Lucas et al. | |
| 2020/0311115 A1* | 10/2020 | Tomberg | G06N 20/00 |
| 2023/0103430 A1* | 4/2023 | Wang | G06N 5/02 |
| | | | 706/12 |
| 2023/0117881 A1* | 4/2023 | Sztyler | G16B 40/20 |
| | | | 706/15 |

FOREIGN PATENT DOCUMENTS

| | | |
|---|---|---|
| KR | 10-2005-0060646 A | 6/2005 |
| KR | 10-1243063 B1 | 3/2013 |
| KR | 10-2017-0065417 A | 6/2017 |
| KR | 10-1875306 B1 | 7/2018 |
| KR | 10-2020-0080571 A | 7/2020 |
| KR | 10-2233464 B1 | 3/2021 |
| WO | 2007/062885 A1 | 6/2007 |
| WO | 2020/065326 A1 | 4/2020 |
| WO | 2020/139861 A1 | 7/2020 |

OTHER PUBLICATIONS

Extended European Search Report issued Jan. 3, 2024 in European Application No. 21856080.3.
International Search Report for PCT/KR2021/009271 dated Nov. 16, 2021 [PCT/ISA/210].
Written Opinion for PCT/KR2021/009271 dated Nov. 16, 2021 [PCT/ISA/237].

* cited by examiner

[FIG. 1]
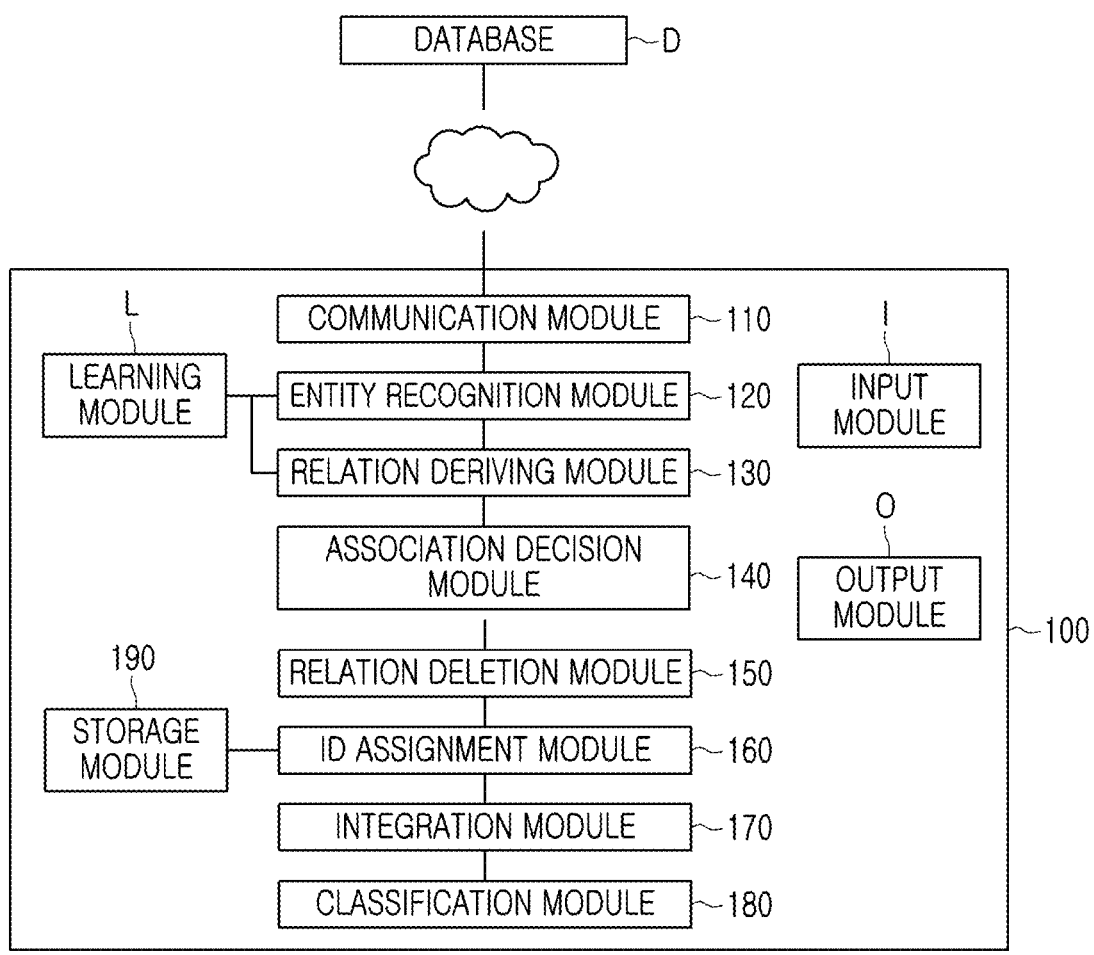

[FIG. 2]

Conventional method detects genes and diseases and their association by sentence.

Sentence 1
Neurotrophic factors (nerve growth factor [ NGF GENE ], brain-derived neurotrophic factor [ BDNF GENE ] and glial-derived neurotrophic factor [ GDNF GENE ]) are growth factors implicated in the growth and differentiation of brain nerve cells.

Sentence 2
In accordance with the role of neurotrophic factors in tumour behaviour the aim of the present study was to investigate their expression in two childhood brain neoplasms DISEASE, namely low-grade astrocytomas DISEASE and ependymomas DISEASE.

Sentence 3
The expression of NGF GENE decreases both in tumour samples and in the CSF of affected children compared with controls.

Unable to detect gene-disease association when the content is described through multiple sentences.

| Sentence no. | Association | Claim |
|---|---|---|
| 1 | N/A | No disease |
| 2 | N/A | No gene |
| 3 | N/A | No disease |

[FIG. 3]
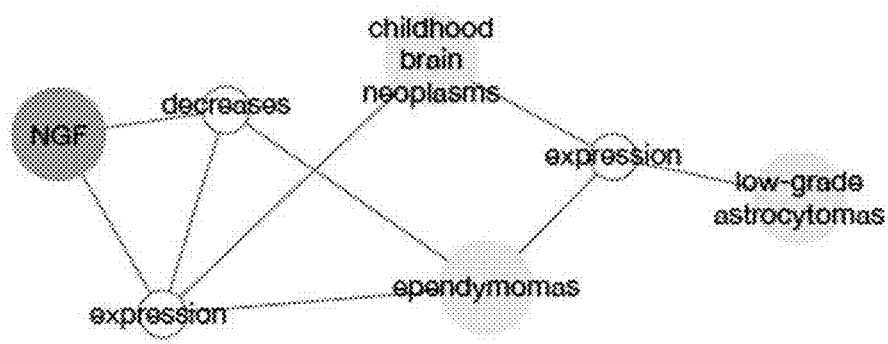

[FIG. 4]

Clinical relevance REG of gain-of-function POSREG mutations VAR of p53 GENE in high-grade serous ovarian carcinoma DISEASE . PURPOSE: Inactivation VAR of TP53 GENE , which occurs predominantly by missense mutations VAR in exons 4-9, is a major genetic alteration REG in a subset of human cancer. In spite of growing evidence that gain-of-function POSREG ( GOF POSREG ) mutations VAR of p53 GENE also have oncogenic activity MPA , little is known about the clinical relevance of these mutations VAR . METHODS: The clinicopathological features of high-grade serous ovarian carcinoma DISEASE (HGS-OvCa) patients with GOF POSREG p53 GENE mutations VAR were evaluated according to a comprehensive somatic mutation profile comprised of whole exome sequencing, mRNA expression, and protein expression profiles obtained from the Cancer Genome Atlas (TCGA). RESULTS: Patients with a mutant

— 3RD ENTITY
— 2ND ENTITY
— 1ST ENTITY

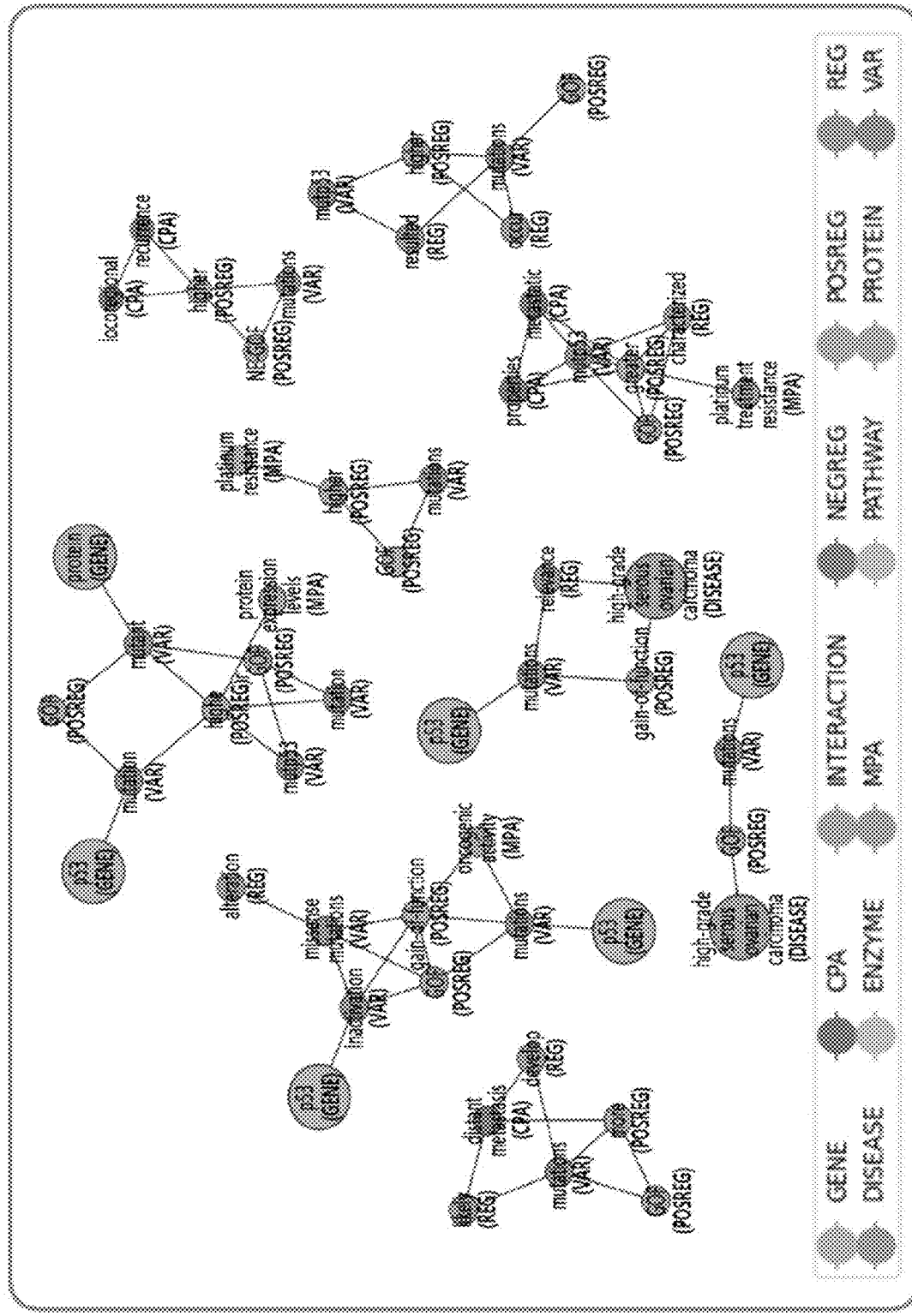
[FIG. 5]

[FIG. 6]

Neurotrophic factors (nerve growth factor [ NGF GENE ], brain-derived neurotrophic factor [ BDNF GENE ] and glial-derived neurotrophic factor [ GDNF GENE ]) are growth factors implicated in the growth and differentiation of brain nerve cells. In accordance with the role of neurotrophic factors in tumour behaviour the aim of the present study was to investigate their expression mRNA in two childhood brain neoplasms DISEASE , namely low-grade astrocytomas DISEASE and ependymomas DISEASE . The expression mRNA of NGF GENE decreases NEGREG both in tumour samples and in the CSF of affected children compared with controls.

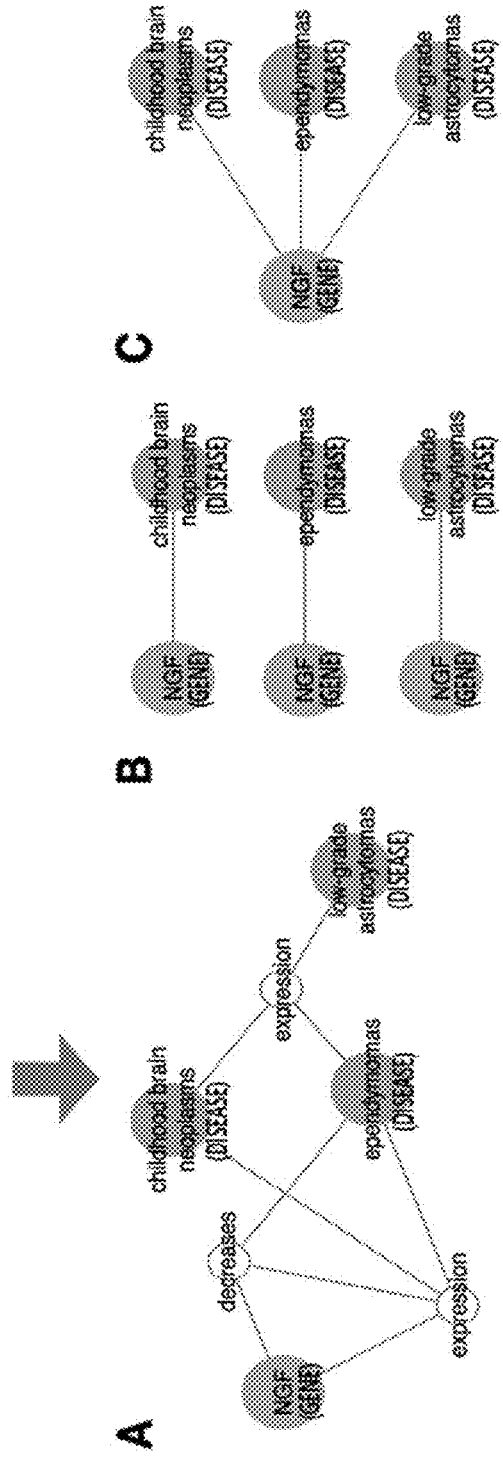

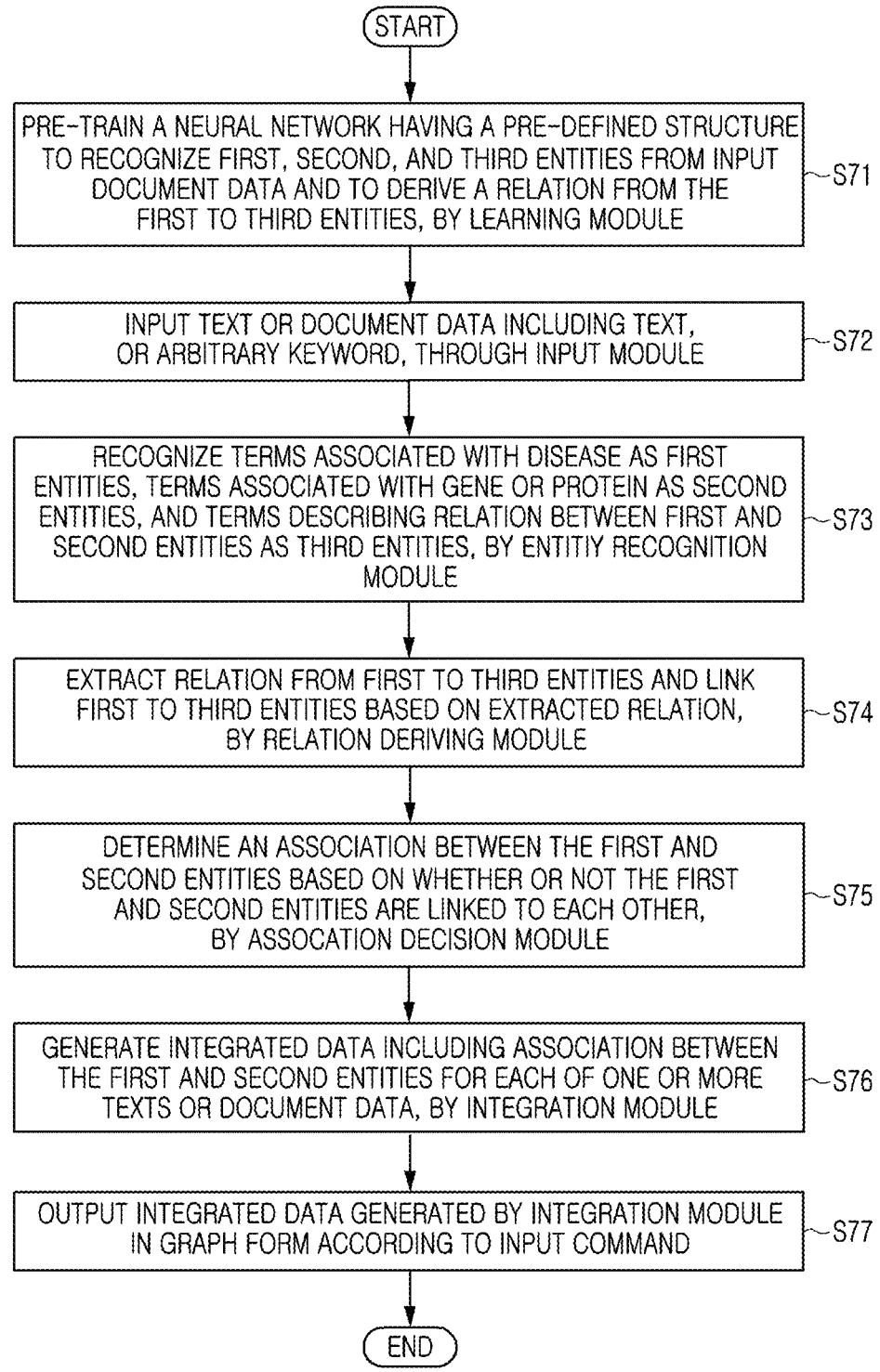

METHOD FOR IDENTIFYING ASSOCIATION BETWEEN DISEASE-RELATED FACTORS FROM DOCUMENT DATA, AND SYSTEM CONSTRUCTED USING SAME

CROSS REFERENCE TO RELATED APPLICATIONS

This application is a National Stage of International Application No. PCT/KR2021/009271 filed Jul. 19, 2021, claiming priority based on Korean Patent Application No. 10-2020-0101764 filed Aug. 13, 2020 and Korean Application No. 10-2020-0176766 filed Dec. 16, 2020.

TECHNICAL FIELD

The present invention relates to a method and a system for recognizing disease-related factors from a plurality of document data, and predicting and identifying an association between the factors, particularly an association between a specific disease and a specific gene or protein.

BACKGROUND

The drug development process involves collecting and organizing a variety of scattered data so as to find gene-to-disease relations or protein-to-disease relations. Today, massive amounts of knowledge data are distributed in atypical text forms, and much effort is required in order to study diseases and genes/proteins in real-time and find the relations between them. Accordingly, a technique for performing natural language processing from atypical texts included in the document data through a device having a computation function (e.g., a computer) has been developed.

According to related arts, the relation between entities is extracted only for the entities contained within a single sentence. There can be cases where all disease-related factors appear in one sentence of document data, but more frequently, the disease-related factors are described across multiple sentences. Although the related art may recognize relations between entities and link the entities according to the recognized relations, it has a problem of low accuracy and low reliability of data because its natural language processing is performed independently on each sentence.

Meanwhile, WO 2020/139861 relates to a knowledge graph in which different characteristics of data (diseases, drugs, etc.) from the heterogeneous datasets are merged into the canonical layer, and relations between data are predicted using a machine learning model. However, the main object of the above patent is to increase the search efficacy by reducing the types and number of data in the process of merging into the canonical layer, and it does not even suggest the idea of recognizing entities and extracting relations between the entities in consideration of the entire text.

Japanese Patent Publication No. 2002-269114 relates to a method for constructing a knowledge database. It proposes extracting objects previously described in a dictionary from lingualized knowledge (text) and quantitatively expressing relation values of the objects included in a plurality of knowledge, thus drawing a graph. However, the above method can only extract objects previously listed in the dictionary and cannot extract objects unlisted in the dictionary, thereby limiting the creation of new data beyond the content of previous data.

Therefore, the inventors propose a system capable of deriving entities and relations between the entities using an artificial intelligence (AI) deep learning technology, from a plurality of document data, by considering the context of the entire text content, the form of the words themselves, and the like, and outputting, in a graph form, data reflecting the recognized entities and association of the entities according to the relation.

(PTL 1) WO 2020/139861 (2020.07.02)
(PTL 2) Japanese Patent Publication No. 2002-269114 (2002.09.20)

SUMMARY

Technical Problem

In order to solve the problems described above, an object of the present invention is to provide a method and a system capable of intuitively checking entities associated with a specific entity by recognizing, from a plurality of document data, terms related to diseases, genes, and proteins, and terms describing the relation between the same, and creating integrated data in a graph form including relations between the entities.

Further, an object of the present invention is to provide a method for constructing a system with high accuracy and reliability and the system because relations between entities are derived by considering the context and meaning of a plurality of sentences included in the document data.

In addition, an object of the present invention is to provide a method and a system capable of outputting entities and relations between the entities in a graph form, thereby enabling intuitively checking on the relations between the entities.

In addition, an object of the present invention is to provide a method and a system for solving a problem of the increased volume of data or extraction of low-importance data, by deleting a relation corresponding to "not associated."

In addition, an object of the present invention is to provide a method and a system capable of categorizing associations between entities according to characteristics of the associations, and separately checking entities associated with a specific entity based on a specific category of associations.

In addition, an object of the present invention is to provide a method and a system capable of recognizing a new range of entities other than existing data, and deriving relations using a pre-trained neural network model during the process of recognizing the entities from document data and deriving the relations.

The objects of the present invention are not limited to those mentioned above, and other objects which are not mentioned above will be clearly understood from the description below.

Technical Solution

According to an embodiment of the present invention for achieving the above object, a method for identifying an association between disease-related factors from document data by extracting disease-related terms, gene-related terms and protein-related terms and extracting relations between the terms using one or more document data, and includes steps of: (a0) pre-training a neural network having a pre-defined structure to recognize first, second, and third entities from a text or a text included in document data input to the neural network and to derive a relation from the first to third entities, using labeled document data as training data where a term referring to disease, a term referring to gene or protein, and a term describing a relation between the term referring to disease and the term referring to gene or protein are labeled as the first entity, the second entity, and the third entity, respectively, by learning module L; (a) recognizing the first, second and third entities from the text or the text included in the document data input to the neural network using the pre-trained neural network in the step (a0), by entity recognition module 120; (b) extracting a relation from the first to third entities from the text or the text included in the document data input to the neural network, and linking the first, second, and third entities based on the extracted relation using the pre-trained neural network in the step (a0), by relation deriving module 130; (c) determining an association between the first and second entities based on whether or not the first and second entities are linked to each other in the step (b), by association decision module 140; and (d) integrating the association between the first and second entities determined in the step (c) for entities in one or more document data to generate integrated data, by integration module 170.

In an embodiment, the relation from the first to third entities is extracted by utilizing either surrounding words that are not recognized as one of the first, second and third entities but are included in the input text or in the text of the input document data or linking words.

In an embodiment, the training data is vectorized labeled data (cotext vector) of the first entity, the second entity, and the third entity.

In an embodiment, after the step (a0) and before the step (a), the method may further include inputting a text or document data including a text, or querying an arbitrary keyword, through input module I, in which, if the arbitrary keyword is queried through the input module I, the step (a) may further include: collecting document data that contains the queried arbitrary keyword and recognizing the first, second, and third entities from the collected document data using the neural network, by the entity recognition module 120, and the step (b) may further include, extracting a relation from the first to third entities from the collected document data using the neural network, by the relation deriving module 130.

In an embodiment, after the step (d), the method may further include (e) outputting the integrated data in a graph form through output module (O), in which the integrated data represent only a relation between the first and second entities determined to be associated, or in addition, any of the intermediate entities linking the first and second entities determined to be associated.

In an embodiment, the step (b) may further include, extracting a relation between the entities using a first relation type representing a theme of the entities or a second relation type representing a causal relation between the entities, by the relation deriving module 130.

In an embodiment, the steps (a) and (b) may be performed on one or more sentences included in the document data, and the step (b) may further include extracting a relation from the first to third entities so as to link the first, second, and third entities to each other, by the relation deriving module 130, wherein from the first to third entities are included in two or more sentences.

In an embodiment, the method may further include, assigning a unique identifier (ID) to each of the first and second entities recognized in step (a), by ID assignment module 160, wherein the assigned ID is uniform across an arbitrary term and; a synonym or an abbreviation of the arbitrary term.

In an embodiment, the method may further include, assigning an ID matching a full name, not an abbreviation, to an arbitrary term, by the ID assignment module 160, if two or more IDs match the arbitrary term.

In an embodiment, the method may further include, deleting a relation matching "not associated" by relation deletion module 150 if the relation between the entities extracted by the relation deriving module 130 includes "not associated".

In an embodiment, the method may further include, in the step (b) further include, linking any one of a plurality of first entities to only one of a plurality of second entities, and then linking another one of the plurality of the first entities to the second entity other than the one linked previously, by the relation deriving module 130, if the plurality of the first entities are linked to the plurality of the second entities in the document data by the relation deriving module 130.

In an embodiment, the method may further include, deleting a recognized entity if the entity is recognized as the first or second entity according to the entity recognition module 120, but is included in a pre-defined set of entities to be ignored.

In an embodiment, the method may further include, after the step (d), classifying the associations between the first and second entities included in the integrated data based on a pre-defined association types with unique characteristics according to classification module 180.

In an embodiment, the term describing a relation between the term referring to disease and the term referring to gene or protein may include one or more terms of variation-related terms, molecular physiological activity-related terms, interaction-related terms, pathway-related terms, cell physiological activity-related terms, regulation-related terms, positive regulation-related terms, and negative regulation-related terms.

In an embodiment, the step (a0) may further include, simultaneously pre-training the neural network to recognize the first, second, and third entities from the input text or the input document data, and the to derive the relation between the first to third entities, by the learning module (L).

In an embodiment, the steps (a) and (b) may be performed simultaneously.

In an embodiment, the step (d) may include: (d1) building unit data by the integration module 170, in which the unit data may be data linked to each other based on the derived relation from the first to third entities recognized from the document data, and (d2) integrating each unit data to generate integrated data by the integration module 170, by combining first or second entities assigned the same ID, and then merging first or second entities linked thereto.

Further, a system constructed using the method described above is provided.

Further, a computer program stored in a computer readable recording medium to execute the method described above is provided.

Advantageous Effects

According to the present invention, it is enabled to intuitively check entities associated with a specific entity by recognizing, from a plurality of document data, terms related to diseases, genes, and proteins, and terms describing relations between the same, and creating integrated data in a graph form including the relations between the entities.

In addition, according to the present invention, a constructed system has high accuracy and reliability because relations between entities are extracted by considering the context and meaning of multiple sentences included in the document data.

In addition, according to the present invention, it is possible to intuitively check relations between entities since the entities and the relations between the entities are visualized in the form of a graph.

In addition, according to the present invention, it is possible to solve a problem of an increased volume of data or extraction of low-importance data, by deleting a relation corresponding to "not associated."

In addition, according to the present invention, it is possible to categorize associations between entities according to the characteristics of the associations, and thus separately check entities associated with a specific entity based on a specific category of associations.

In addition, according to the present invention, it is possible to recognize a new range of entities and to derive a new range of relations other than the existing range of data, by using a pre-trained neural network model while recognizing the entities from document data and deriving the relations.

In addition, according to the present invention, it is possible to recognize the first to third entities from document data only by labeling terms corresponding to the first, second or third entities, without labeling grammatical information such as parts of speech and syntactic information to the document data. Accordingly, since the present invention performs named entity recognition without defining separately part-of-speech information, terminology dictionary, terminology rules, etc. for each document data, it provides processing with excellent efficiency.

In addition, according to the present invention, since training is carried out in a manner such that the process of recognizing entities from input document data and the process of deriving relations between the recognized entities are performed simultaneously, the entities can be recognized and the relations can be derived with increased accuracy, compared to the related art method in which the entity recognition and interaction derivation between the entities are sequentially performed.

In addition, according to the present invention, since the relation from the recognized first to third entities is extracted using either surrounding words that are not recognized as one of the first, second, and third entities but are included in the text or linking words, the relation can be extracted with high accuracy.

BRIEF DESCRIPTION OF THE DRAWINGS

FIG. 1 is a block diagram that explains a system constructed according to an embodiment of the present invention.

FIG. 2 is a diagram that explains recognizing entities from document data and deriving relations between the entities in the related art.

FIG. 3 is a diagram that explains recognizing entities from document data and deriving relations between the entities according to an embodiment of the present invention.

FIG. 4 is a view illustrating entity recognition from document data different from the document data of FIG. 3, according to an embodiment of the present invention.

FIG. 5 is a diagram provided to explain that entities are connected to each other based on relations derived between the entities recognized in FIG. 4.

FIG. 6 is a view illustrating aspects of a state in which entities are connected to each other with the relations extracted from the document data of FIG. 3, in accordance with an embodiment of the present invention. Specifically, FIG. 6-A illustrates data in a graph form that can be generated from text or document data, FIG. 6-B illustrates data in a graph form showing the association between the first and second entities according to whether the first and second entities are linked in FIG. 6-A, and FIG. 6-C illustrates data in a graph form represented after deleting overlapping entities in FIG. 6-B.

FIG. 7 is a flowchart provided to explain a method according to an embodiment of the present invention.

DETAILED DESCRIPTION

Hereinafter, the present invention will be described in detail with reference to the attached drawings.

The term "document data" as used herein refers to data formed of text, and the text may include all the currently used languages such as English, Chinese, Japanese, and Korean.

Referring to FIG. 1, system 100 according to the present invention includes communication module 110, entity recognition module 120, relation deriving module 130, association decision module 140, relation deletion module 150, ID assignment module 160, integration module 170, classification module 180, storage module 190, input module I, output module O, and learning module L.

The communication module 110 is configured to enable the system 100 according to the invention to communicate with an external system. In an example, the system 100 may be wirelessly connected to an external system through a communication network, or may communicate with the external system through wired communication.

The system 100 according to the invention may perform mutual communication with database D, in which the database D may be an open database or private database, and conceptually refers to a database including a research paper database, a medical information database, a pharmaceutical information database, a search portal database and the like.

The entity recognition module 120 is configured to recognize entities from texts or texts included in the text-including document data input through the input module I according to a preset method. The document data from which the entities are recognized may be a research paper, for example, and specifically, it may be an abstract of a research paper, but not limited thereto.

When an arbitrary keyword is input through the input module I (i.e., when a specific keyword is input in a search box provided in the system), the document data, which is stored in the database D and which includes the input keyword, may be searched, and it is possible to collect the searched document data and extract entities and relation between the entities from the collected data. More specifically, the document data may be research paper data, and the information included in the research paper data may be extracted by securing unique IDs assigned to each research paper data and querying the secured IDs to the entity recognition module 120.

Recognizing the entities by the entity recognition module 120 may be performed using a neural network model having a pre-defined structure, which will be described in greater detail below.

The entity recognition module 120 is configured to recognize disease-related terms included in the document data as first entities, and recognize gene-related terms and protein-related terms as second entities, respectively.

In an example, the disease-related terms may be, for example, Alzheimer's disease, frontotemporal dementia, frontotemporal lobar degeneration, congenital diarrhea, asthma, male infertility, cancer, atopic dermatitis, earlyonset AF, and chronic liver disease, and may include any term that refers to a specific disease.

Further, the gene-related terms may be, for example, p53, PCSK9, FLG, CgPDR1, STAT1, KMT2A, LRRK2, SHP-2, TRPV1, and NR2F2, and may include any term that refers to a specific gene.

Further, the protein-related terms may be, for example, APC protein, G protein-coupled receptors, LDL receptor, p53 protein, KRIT1 protein, H4 histones, CES1 protein, G protein, heterotrimeric Gs protein, apolipoprotein C-III, lipoprotein lipase, methyltransferase enzyme, phosphatase, zeaxanthin epoxidase, luciferase, GlcNAc-1-phosphotransferase, methyltransferases MLL1, acetyltransferase MOZ, tyrosine kinase Axl, and LasA protease, and may include any term that refers to a specific protein.

Further, the entity recognition module 120 is configured to recognize the terms related to variation, molecular physiological activity, interaction, pathway, cell physiological activity, regulation, positive regulation, and negative regulation, which are included in the document data, as third entities.

However, aspects are not limited to the above, and the third entity may be any term that describes the relation between the first and second entities.

In an example, the variation-related terms may be, for example, mutation, mutant, variants, E76K, mutp53, deletion, loss, frameshift, haploinsufficiency, and GOF p53, and may include any term that means a variation or any term that refers to a specific material in which variation occurs.

Further, the molecular physiological activity-related terms may be, for example, expression, activity, function, signaling, phosphorylation, acetylation, bioactivation of cyclophosphamide, LPL protein level, triglyceride catabolism, and sustained exocytosis in MB neurons, and may include any term that means molecular physiological activity or any term that refers to molecular physiological activity of a specific material.

Further, the interaction-related terms may be, for example, binding, interaction, agonist binding, DNA-binding, functional interaction, combined, and binding capacity of APRIL ligand to B cells, and may include any term that means interaction between two entities.

Further, the pathway-related terms may be, for example, EGFR/PI3K/AKT pathway, epidermal growth factor receptor (EGFR)/phosphatidylinositol 3-kinase (PI3K)/AKT pathway, ERK pathway, IL-3-induced Erk and phosphatidylinositol 3-kinase (PI3K) pathway, PI3K pathway, JNK Signaling, cAMP pathway, Wnt pathway, mitogen-activated protein kinase (MAPK) pathway, and yeast-based signaling pathway, and may include any term that refers to pathway associated with the expression of a specific disease.

Further, the cell physiological activity-related terms may be tumorigenesis, autophagy, cell migration, proliferation, tumor malignancy, developmental defects, tumor development, apoptosis, migration, and distant metastasis, and may include any term that has the meaning of cell physiological activity or any term that refers to physiological activity of a specific cell.

Further, the regulation-related terms may be cause, associate, lead to, affect, alter, influence, induce, contribute, modulate, and change, and may include any term that refers to a term in which one entity affects another entity.

Further, the positive regulation-related terms may be increase, enhance, elevate, higher, promote, and activation, and may include any term that has the meaning of promoting the expression of a specific material.

Further, the negative regulation-related terms may be reduce, decrease, impair, diminish, prevent, absence, disrupt, and lack, and may include any term that has the meaning of suppressing the expression of a specific material.

The relation deriving module 130 is configured to extract a relation from the first to third entities recognized by the entity recognition module 120 and link the first to third entities according to the extracted relation.

When the first to third entities are linked to each other by the relation deriving module 130, it means that the linked entities are associated with each other in a certain sense.

The relation deriving module 130 according to the invention derives the relation from the first to third entities in consideration of all the texts (sentences) included in one document data.

The relation deriving module 130 according to the invention may extract the relation from the first to third entities according to context of the terms (words) (words such as "result in" or "cause") that are not recognized by the entity recognition module 120 or a form that words are linked.

Referring to FIGS. 2 and 3, this will be described in more detail.

In the related art, even if one document data includes a plurality of sentences, relations between entities are extracted in consideration of only one sentence.

For example, referring to FIG. 2, only the gene-related terms such as NGF, BDNF, and GDNF may be recognized from Sentence 1, and only the disease-related terms such as childhood brain neoplasms, low-grade astrocytomas, and ependymomas may be recognized from Sentence 2, and only the gene-related terms such as NGF may be recognized from Sentence 3. In the related art, since the relations between entities are extracted from only one sentence, rather than a plurality of sentences, including Sentences 1, 2, and 3, it is not possible to extract any relation from the document data illustrated in FIG. 2.

Meanwhile, the relation deriving module 130 according to the invention extracts the relation by considering all sentences included in document data.

In the same document data, by considering all of Sentences 1, 2, and 3, the relation deriving module 130 extracts that NGF has an "expression" or "decrease" relation with ependymomas, childhood brain neoplasms, or low-grade astrocytomas. As such, the system constructed according to the invention has high accuracy and reliability, since the relation is extracted by considering the context and meaning of the sentences included in the document data as a whole.

According to another example, it is assumed that the text includes the sentence "When the expression of gene A is reduced, the symptoms of disease B are alleviated" and the sentence "gene A strengthens the function of gene C."

In the related art, since only one sentence is considered, it is possible to derive the relation between A-B and the relation between A-C (i.e., the relation of "A-expression-reduction-B-alleviation," and the relation of "A-strengthening-C"), but it is difficult to derive the relation between B-C.

Meanwhile, in the present invention, since it is possible to take into consideration the context of the entire text, it is possible to extract the relation of "C-strengthening-A-expression-reduction-B," and as a result, extract the relation between B-C.

Meanwhile, the first to third entities in the document data may be labeled with different colors (or shapes such as hatching, etc.) to be marked. In a graph representing the first to third entities and the relations therebetween, the first and second entities may be expressed as figures (e.g., circles) that are more prominent than the third entity. The first and second entities correspond to the diseases and genes/proteins, respectively, and may be expressed as figures larger than the other entities, which is advantageous because it allows one to easily find the locations of the diseases and genes/proteins on the graph and determine whether these are associated with each other.

The relations extracted by the relation deriving module 130 include a first relation type indicating a theme of an entity and a second relation type indicating a causal relation between entities.

For example, if document data includes the text "Gene A has Mutation B" and the text "Regulation B occurs in Disease A," it means a theme in which the gene A has the mutation B and a theme in which the regulation B occurs in the disease A, and accordingly, the relation deriving module 130 extracts the first relation type indicating the "theme" of the entities.

Meanwhile, even when the document data does not include a sentence clearly describing the relation between the first and second entities, the relation deriving module 130 is still able to extract the relation between the first and second entities.

For example, for the text "PNPLA3 I148M polymorphism" in document data, it is possible to extract a relation in which the mutation I148M is in the gene PNPLA3.

In addition, if document data includes the texts "Loss of Function B occurs due to Mutation A" and "Biological activity B increases when the expression of Gene A is reduced," the relation deriving module 130 extracts the second relation type indicating a "causal relation" as the relation between these entities, since the texts mean that the occurrence of Mutation A causes the loss of Function B and that the biological activity B becomes higher as the expression of the gene A is lowered.

In an embodiment of the invention, recognizing the entity by the entity recognition module 120 and deriving the relation by the relation deriving module 130 may be performed simultaneously.

The association decision module 140 is configured to determine the association between the first and second entities using the relation derived by the relation deriving module 130.

That is, the association decision module 140 determines whether the entities are associated with each other, based on whether or not the first and second entities are linked to each other according to the relation extracted by the relation deriving module 130.

Referring to FIG. 3 as an example, the second entity "NGF" is connected to the first entity "ependymomas" through the third entity "decrease," and therefore, the association decision module 140 may determine that "NGF" and "ependymomas" are associated with each other. Further, "NGF" is connected to the first entity "childhood brain neoplasms" through the third entity "expression," and thus, "NGF" may be determined to be associated with "childhood brain neoplasms."

As such, the association decision module 140 determines the association between the first and second entities according to whether or not the first and second entities recognized from the document data are linked to each other based on the derived relation.

The relation deletion module 150 is configured to delete a relation corresponding to "not associated," when the relation extracted by the relation deriving module 130 includes a "not associated" relation.

Examples will be described in more detail below based on the assumption that the document data includes the text "Gene A is not associated with Disease B," and the entity recognition module recognizes the second entity "A," the first entity "B," and the third entity "associated."

In this case, the entities "A," "B," and "associated" may be linked to each other through a relation. However, if the relation "not associated" is extracted as a relation, there is a risk of additionally deriving a relation in which the entities "C" and "D" are not associated with the entity "B" when the entities "C" and "D" are derived as linked to the entity A according to the derived relation of "A."

Therefore, if the relation extracted by the relation deriving module 130 is "not associated," that is, for example, if terms such as "no" or "not" are detected in a location close to "associated" in the process of extracting the entity "associated," the relation deletion module 150 deletes the relation corresponding to "not associated" by assuming that the entities "A" and "B" are linked by the relation "not associated." It is thus possible to solve the problem of the voluminous data or extraction of low-importance data (for example, "an entity is not associated with another entity" is likely to be determined to be of low importance).

The ID assignment module 160 is configured to assign a unique identifier (ID) to each of the first and second entities recognized by the entity recognition module 120.

That is, the ID assignment module 160 according to the invention assigns a unique ID to arbitrary terms that fall into the first or second entity category. It assigns the same ID to the terms that can be determined to be the same as an arbitrary term, such as the synonyms or abbreviations of the arbitrary term.

Meanwhile, two or more IDs may be assigned to an arbitrary term that falls under the category of the first or second entity recognized by the entity recognition module 120. For example, "alpha-fetoprotein" is also referred to by its abbreviation "AFP," and both "alpha-fetoprotein" and "AFP" may be assigned the ID 174. [123]"AFP" also corresponds to a synonym for the gene "TRIM26," that is, "AFP" may also be assigned the ID 7726, which is the same as that of "TRIM26."

That is, "AFP" may be assigned with two IDs, 174 and 7726, and in this case, the ID assignment module 150 assigns, as the ID of "AFP," the ID matching the full name of "AFP," rather than the ID 7726 matching the abbreviation.

When assigning IDs by the ID assignment module 160 is completed, unit data having a graph form as illustrated in FIG. 3 may be generated from each document data.

In an example, the unit data may be visualized as graphs that represent the relations from the first to third entities recognized from one document data. In another example, it may be a graph representing only the relation between the first and second entities. In yet another example, it may be the form of a graph representing the relation between the first and second entities after merging the entities having the same ID into a single entity (see FIG. 6).

The integration module 170 is configured to integrate the unit data to generate integrated data including the association of all the first and second entities recognized from the document data.

Considering that the integrating process by the integration module 170 can be performed more accurately and quickly as the smaller and simpler unit data used for integration is, it is preferable to generate the integrated data using the unit data in the form of C in FIG. 6.

The integration module 170 may also perform a process of merging entities that are included in each unit data and have the same ID into one entity, and accordingly, a single integrated graph reflecting all of a plurality of document data may be generated.

The classification module 180 is configured to classify associations according to unique characteristics between the first and second entities using the integrated graph generated by the integration module 170.

For example, if "Gene A" and "Disease B" are linked to each other through the relation "variation," the classification module 180 categorizes the association between A and B into the first association type "gene mutation."

Further, if "Gene A" and "Disease B" are connected to each other through the relations "molecular physiological activity" or "negative regulation" (or "positive regulation"), the classification module 180 categorizes the association between A and B into the second association type "change in physiological activity."

However, aspects are not limited to the above, and the classification module 180 may classify the association between the first and second entities according to their unique characteristics, and it is also possible to check entities linked to the entity "A" with a specific association type by user's choice.

In the storage module 190, the first and second entities with a unique ID mapped are stored, and terms corresponding to entities to be ignored are stored.

That is, the ID assignment module 160 assigns a unique ID to each of the first and second entities recognized by the entity recognition module 120, and specifically, assigns matched ID to each of the first and second entities stored in the storage module 190.

In addition, if the first or second entities recognized by the entity recognition module 120 correspond to the entities to be ignored that are stored in the storage module 190, the corresponding entities are deleted. The entities to be ignored may include the terms which are likely to be determined to be the abbreviations of the second entity (gene) in view of the form of the terms, such as DNA, RNA, rDNA, mRNA, etc., but do not correspond to the second entity. Likewise, they may also include the terms which are likely to be determined to be the abbreviations of the first entity, but do not correspond to the first entity.

Recognizing the first to third entities by the entity recognition module 120 and deriving the relation by the relation deriving module 130 according to the invention may be performed using a pre-trained neural network model.

The neural network model has a pre-defined structure and includes an encoder and a decoder.

In an example, the encoder may be any pre-trained neural network model such as Bidirectional Encoder Representations from Transformers (BERT) or Generative Pre-Training (GPT), and the decoder may be a model such as a feed-forward neural network, a convolutional neural network, or a recurrent neural network, where the normalization technology such as layer normalization and dropout may be applied.

In addition, the training process according to the invention may be performed through the following steps.

First, inputting document data is performed, in an example, the document data may be a research paper, and specifically, an abstract of the research paper is input. In the input document data, the first to third entities may have been labeled respectively.

Then, the text of the abstract is tokenized. The term "tokenize" as used herein refers to a process by which a computer can identify the meaning of a text and process it, and it means a process of separating the text into a minimum size of meaningful data.

Then, the result data of tokenization is input to the pre-trained encoder, and the context vectors output from the encoder are input to the decoder to train so that, within the text, recognizing the first to third entities and deriving the relations from the first to third entities are performed. In this case, the training may be performed to recognize the entities and derive the relations are performed simultaneously rather than sequentially.

Training the neural network model may be completed according to the above process, and the entity recognition module 120 and the relation deriving module 130 are configured to recognize the entities and derive the relations from the document data using the pre-trained neural network model.

It is to be noted that, according to the invention, aspects are not limited to the neural network model described above, and any neural network model that can be implemented through pre-training so as to recognize the first to third entities from the input text and derive the relations may be applied.

According to the related art, after storing terms to be recognized in advance in an index dictionary, pre-stored terms are recognized from texts. In this case, if the term included in the text has not been previously stored in the index dictionary, the term cannot be recognized, and eventually, the system may be constructed only within a previously known range.

However, according to the invention, instead of recognizing the terms stored in the index dictionary, the neural network model is trained with training data that is labeled to indicate which part of the text corresponds to the first, second, or third entity. Accordingly, it is possible to infer and recognize even the terms not trained in advance, by considering the form or context of the terms. Therefore, it is possible to recognize not only entities and relations between the entities known through previously published papers, but also a new scope of entities and relations.

The input module I may have the form of an input device such as a touch panel or a keyboard, but is not particularly limited to the above as long as it is in such a form that can receive inputs of user commands and transmit the command to the system according to the invention.

Further, the output module O may have the form of an output device such as a monitor or a display panel, but is not particularly limited to the above as long as it is in such a form that enables a visual check on the calculation result of the system according to the invention.

The command input through the input module I (e.g., arbitrary text, document data including texts, arbitrary keywords) may be input or queried. The entities may be recognized from the input text, the input document data, and papers including the arbitrary keywords, and the relations between the recognized entities may be derived so as to determine the association between the entities based on the derived result. The determined association between the entities may be output through the output module O in the form of a graph.

According to the invention, a graph (in the form of FIG. 6-C) showing only the simple relations between the first and second entities may be output, and as illustrated in FIGS. 5 and 6-A, the basis (other entities included in the relation between the first and second entities) for determining that the first and second entities are associated may be output together in a graph form, in which case it is possible to intuitively check the context used to determine the association.

The system according to the invention can provide various types of information in addition to the information described above.

For example, it is possible to provide information on the time of publishing the document data from which the relation between a specific disease-gene pair is extracted, the frequency of deriving the association of the specific disease-gene pair from document data, and so on. It is possible to provide the information on relations for all the entity-entity pairs, rather than being limited to disease-gene pairs.

In an example, the document data may be a research paper, and it is possible to check the research trends because the system according to the invention provides the information on the publication time of the document data from which the relations of specific disease-gene pairs are derived. (For example, if paper data discussing the relationship between a specific disease-gene pair was intensively published at a particular time, it can be confirmed that the research on this disease-gene pair was actively conducted at that time.)

Further, in the system according to the invention, it is possible to check the importance of the relation between a specific disease-gene pair by providing the frequency of document data from which the relations are derived. (For example, if the number of document data from which relations of a specific disease-gene pair are derived is far greater than the number of document data from which relations of another disease-gene pair are derived, it can be confirmed that the importance of the specific disease-gene pair is higher.)

Hereinafter, a method according to the invention will be described in detail with reference to FIG. 7.

First, the system 100 pre-trains, by the learning module L, a neural network model with a pre-defined structure so as to recognize the first to third entities from the document data and derive relations from the first to third entities, at S71.

In an embodiment of the invention, pre-training the neural network model to recognize the first to third entities from the document data and another pre-training the neural network model to derive the relation from the first to third entities may be sequentially performed. In another embodiment, pre-training the neural network model to recognize the first to third entities from the document data and another pre-training the neural network model to derive the relation from the first to third entities may be performed simultaneously.

The training data may be the document data in which the first, second, and third entities are labeled respectively. As pre-training is performed, the entity recognition module 120 and the relation deriving module 130 of the system 100 can recognize the first to third entities from a large number of atypical texts (queried arbitrary text, document data, etc.) using the neural network model, and derive the relation between the entities simultaneously. Accordingly, it is possible to extract the information on the association between disease and gene/protein comprehensively and efficiently.

Then, texts, document data including texts, or arbitrary keywords are input or queried through the input module I, at S72.

Then, the entity recognition module 120 recognizes the first and second entities which are the terms related to diseases, genes, and proteins from the texts, the document data, or a research paper including the arbitrary keyword using the neural network model, and recognizes the terms describing the relation between the first and second entities as the third entities from the text included in the document data, at S73. Then, the relation deriving module 130 extracts the relation from the first to third entities in consideration of a plurality of sentences, and links the first, second, and third entities according to the extracted relation, at S74.

In an example, when the entities recognized by the entity recognition module 120 correspond to the terms to be ignored which are stored in the storage module 190 in advance, the corresponding entities may be deleted.

Further, when the relation derived by the relation deriving module 130 corresponds to "not associated," the relation deletion module 140 deletes the relation corresponding to "not associated."

The association decision module 140 determines the association between the first and second entities based on whether the first and second entities are linked to each other through the extracted relation at S75.

Then, the ID assignment module 160 of the system 100 assigns a unique ID to each of the recognized first and second entities.

Unique IDs are matched (mapped) to each of the first and second entities and stored in the storage module 190 (that is, information including a first entity-ID pair and a second entity-ID pair is stored), and the ID assignment module 160 assigns IDs to the entities recognized using the above information and n-gram technology.

When assigning the IDs by the ID assignment module 160 is completed, the unit data as shown in FIGS. 5 and 6 may be generated using the entities recognized from each document data and the relations between the entities.

The integration module 170 of the system 100 integrates a plurality of unit data to generate integrated data, at S76. For example, the entities are collected after removing the overlap of the entities with the same ID, and then likewise relation overlapping is removed so that the integrated data reflecting the information extracted from a plurality of document data may be generated.

In an example, the integrated data may be in the form of a graph as illustrated in FIGS. 5 and 6, and accordingly, it is possible to intuitively check the entities associated with a specific entity.

The classification module 180 of the system 100 categorizes the associations between the entities according to their characteristics using the integrated data. For example, if "Gene A" and "Disease B" are linked to each other through the relation "variation," the classification module 180 classifies the relation between A and B into the first association type "gene mutation." Aspects are not limited to the above, and the classification module 180 may classify the corresponding association into any one of the first to nth association types according to the characteristics of the relations between the entities.

Accordingly, it is possible that the user checks only the entities linked to arbitrary disease by a specific category.

All or at least part of the configuration of the system according to the invention may be implemented in the form of hardware module or software module, or may be implemented in combination of hardware module and software module.

In an example, the software module may be understood as, for example, commands executed by a processor controlling calculation within the system, and such commands may be in such a form that is loaded into a memory within the system.

The method described above for identifying an association between disease-related factors from document data according to the invention may be implemented in the form of program instructions that can be executed through various computer means and recorded on a computer readable medium. The computer readable medium may include program instructions, data files, data structures, and the like alone or in combination. The program instructions recorded on the medium may be those specially designed and configured for the purposes of the present disclosure, or may be known and available to those skilled in computer software. Examples of computer readable recording medium include magnetic media such as hard disks, floppy disks, and magnetic tape, optical media such as CD-ROMs and DVDs, magneto-optical media such as floptical disks, and hardware devices specifically configured to store and execute program instructions such as ROM, RAM, flash memory, and the like. Examples of the program instructions include machine language codes such as those generated by a compiler, as well as high-level language codes that may be executed by a computer using an interpreter, and so on. The hardware device described above may be configured to operate as one or more software modules in order to perform the operations according to the present disclosure, and vice versa.

Although the above has been described with reference to a preferred embodiment of the present disclosure, those skilled in the art will appreciate that various modifications and changes can be made to the present disclosure without departing from the spirit and scope of the present disclosure described in the following claims.

DESCRIPTION OF REFERENCE NUMERALS

100: System
110: Communication module
120: Entity recognition module
130: Relation deriving module
140: Association decision module
150: Relation deletion module
160: ID assignment module
170: Integration module
180: Classification module
190: Storage module
I: Input module
O: Output module
L: Learning module

The invention claimed is:

1. A method for identifying a gene-to-disease or protein-to-disease association, the method comprising steps of:
   (a0) pre-training a neural network having a pre-defined structure to recognize first, second, and third entities from a text or a text included in document data input to the neural network and to derive a relation from the first to third entities, using labeled document data as training data where a term referring to disease, a term referring to gene or protein, and a term describing a relation between the term referring to disease and the term referring to gene or protein are labeled as the first entity, the second entity, and the third entity, respectively, by a learning module;
   (a) recognizing the first, second, and third entities from the text or the text included in the document data input to the neural network using the pre-trained neural network in the step (a0), by an entity recognition module;
   (b) extracting a relation from the first to third entities from the text or the text included in the document data input to the neural network, and linking the first, second, and third entities based on the extracted relation using the pre-trained neural network in the step (a0), by a relation deriving module;
   (c) determining an association between the first and second entities based on whether or not the first and second entities are linked to each other in the step (b), by an association decision module; and
   (d) integrating the association between the first and second entities determined in the step (c) for entities in one or more document data to generate integrated data, by an integration module,
   wherein the training data is vectorized labeled data of the first entity, the second entity, and the third entity,
   wherein the step (a0) further comprises simultaneously pre-training the neural network to recognize the first, second, and third entities from the input text or the input document data and to derive the relation from the first to third entities, by the learning module, and
   wherein the steps (a) and (b) are performed simultaneously.

2. The method of claim 1, wherein the relation from the first to third entities is extracted by utilizing either surrounding words that are not recognized as one of the first, second and third entities but are included in the input text or in the text of the input document data or linking words.

3. The method of claim 1, further comprising:
   after the step (a0) and before the step (a),
   inputting a text or document data including a text, or querying an arbitrary keyword, through an input module,
   wherein, if the arbitrary keyword is queried through the input module I, the step (a) further comprises collecting document data that contains the queried arbitrary keyword and recognizing the first, second, and third entities from the collected document data using the entity recognition module, and
   the step (b) further comprises extracting a relation from the first to third entities from the collected document data using the relation deriving module 130.

4. The method of claim 1, further comprising:
   after the step (d),
   (e) visualizing the integrated data in a graph form through an output module, wherein the integrated data represent only a relation between the first and second entities determined to be associated, or, in addition, any of the intermediate entities linking the first and second entities determined to be associated.

5. The method of claim 1, wherein the step (b) further comprises extracting a relation between the entities using a first relation type representing a theme of the entities or a second relation type representing a causal relation between the entities, by the relation deriving module.

6. The method of claim 1, wherein the steps (a) and (b) may be performed on one or more sentences included in the document data, and
   the step (b) further comprises extracting a relation from the first to third entities so as to link the first, second, and third entities to each other, by the relation deriving module, wherein from the first to third entities are included in two or more sentences.

7. The method of claim 1, comprising:
   assigning a unique identifier (ID) to each of the first and second entities recognized in the step (a), by an ID assignment module, wherein the assigned ID is uniform across an arbitrary term and a synonym or an abbreviation of the arbitrary term.

8. The method of claim 7, further comprising:
assigning an ID matching a full name, not an abbreviation, to an arbitrary term, by the ID assignment module, if two or more IDs match the arbitrary term.

9. The method of claim 1, further comprising:
deleting a relation matching "not associated" by relation deletion module if the relation between the entities extracted by the relation deriving module includes "not associated".

10. The method of claim 1, wherein the step (b) further comprises linking any one of a plurality of first entities to only one of a plurality of second entities, and then linking another one of the plurality of the first entities to the second entity other than the one linked previously, by the relation deriving module, if the plurality of the first entities are linked to the plurality of the second entities in the document data by the relation deriving module.

11. The method of claim 1, further comprising:
deleting a recognized entity if the entity is recognized as the first or second entity according to the entity recognition module, but is included in a pre-defined set of entities to be ignored.

12. The method of claim 1, further comprising:
after the step (d),
classifying the associations between the first and second entities included in the integrated data based on a pre-defined association types with unique characteristics according to classification module.

13. The method of claim 1,
wherein the term describing a relation between the term referring to disease and the term referring to gene or protein includes one or more terms of variation-related terms, molecular physiological activity-related terms, interaction-related terms, pathway-related terms, cell physiological activity-related terms, regulation-related terms, positive regulation-related terms, and negative regulation-related terms.

14. The method of claim 7,
wherein the step (d) comprises:
(d1) building unit data by the integration module, wherein the unit data is data linked to each other based on the derived relation from the first to third entities recognized from the document data; and
(d2) integrating each unit data to generate the integrated data by the integration module, by combining first or second entities assigned the same ID, and then merging first or second entities linked thereto.

15. A system performing the method according to claim 1.

16. A non-transitory computer program stored in a computer-readable recording medium for executing the method according to claim 1.

* * * * *